(12) United States Patent
Chen

(10) Patent No.: US 10,197,696 B2
(45) Date of Patent: Feb. 5, 2019

(54) NMR LOGGING INTERPRETATION OF SOLID INVASION

(71) Applicant: Jinhong Chen, Katy, TX (US)

(72) Inventor: Jinhong Chen, Katy, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 1337 days.

(21) Appl. No.: 14/081,218

(22) Filed: Nov. 15, 2013

(65) Prior Publication Data

US 2015/0142316 A1 May 21, 2015

(51) Int. Cl.
*G01V 1/40* (2006.01)
*G01V 3/32* (2006.01)

(52) U.S. Cl.
CPC ..................................... *G01V 3/32* (2013.01)

(58) Field of Classification Search
None
See application file for complete search history.

(56) References Cited

U.S. PATENT DOCUMENTS

| | | | | |
|---|---|---|---|---|
| 4,933,638 A * | 6/1990 | Kleinberg | ............ | G01N 24/081 324/303 |
| 5,055,788 A * | 10/1991 | Kleinberg | ............ | G01N 24/081 324/303 |
| 5,696,448 A * | 12/1997 | Coates | ...................... | G01V 3/32 324/303 |
| 5,936,405 A * | 8/1999 | Prammer | ............. | G01N 24/081 324/303 |
| 6,005,389 A * | 12/1999 | Prammer | ............. | G01N 24/081 324/300 |
| 6,052,649 A * | 4/2000 | Goldman et al. | ................ | 702/11 |
| 6,424,919 B1 * | 7/2002 | Moran et al. | ..................... | 702/6 |
| 6,439,046 B1 * | 8/2002 | Kruspe et al. | ............. | 73/152.01 |
| 6,518,758 B1 * | 2/2003 | Speier | .................. | G01N 24/081 324/303 |
| 6,545,471 B2 | 4/2003 | Wollin | | |
| 6,603,310 B2 | 8/2003 | Georgi et al. | | |
| 6,808,028 B2 | 10/2004 | Woodburn et al. | | |
| 7,164,267 B2 * | 1/2007 | Prammer | .................. | G01V 3/32 324/300 |
| 7,221,158 B1 | 5/2007 | Ramakrishnan | | |
| 7,227,355 B2 | 6/2007 | Chen et al. | | |

(Continued)

OTHER PUBLICATIONS

W.E. Kenyon, "Petrophysical Principles of Applications of NMR Logging," Mar.-Apr. 1997, The Log Analyst.*

(Continued)

*Primary Examiner* — John Breene
*Assistant Examiner* — Leonard S Liang
(74) *Attorney, Agent, or Firm* — Cantor Colburn LLP

(57) ABSTRACT

A method for estimating an effect on nuclear magnetic resonance (NMR) measurements of an invasion of solid particles into pores of an earth formation penetrated by a borehole includes conveying a carrier through the borehole and performing an NMR measurement on a volume of interest in the formation to provide a relaxation time constant using an NMR tool disposed at the carrier. The method further includes receiving information describing the solid particles in the pores and quantifying, using a processor, an effect on the measured relaxation time constant due to the invasion of solid particles using the received information.

20 Claims, 4 Drawing Sheets

(56) References Cited

U.S. PATENT DOCUMENTS

| | | | |
|---|---|---|---|
| 7,733,086 B2 | 6/2010 | Prammer et al. | |
| 9,617,851 B2* | 4/2017 | Dahl | E21B 49/005 |
| 2005/0104587 A1* | 5/2005 | Akkurt | G01N 24/081 |
| | | | 324/303 |
| 2005/0272158 A1* | 12/2005 | Galford | G01N 24/08 |
| | | | 436/29 |
| 2006/0290350 A1* | 12/2006 | Hursan | G01N 24/08 |
| | | | 324/303 |
| 2008/0272773 A1* | 11/2008 | Romero | G01N 24/081 |
| | | | 324/300 |
| 2009/0195246 A1* | 8/2009 | Jebutu | G01V 3/32 |
| | | | 324/303 |
| 2009/0248311 A1* | 10/2009 | Coope | G01N 24/084 |
| | | | 702/13 |
| 2009/0292473 A1* | 11/2009 | Kruspe | G01V 3/32 |
| | | | 702/8 |
| 2010/0088033 A1* | 4/2010 | Chen | G01N 24/081 |
| | | | 702/8 |
| 2010/0139386 A1* | 6/2010 | Taylor | E21B 47/0003 |
| | | | 73/152.23 |
| 2011/0025324 A1* | 2/2011 | Fransson | G01N 24/081 |
| | | | 324/307 |
| 2011/0181277 A1* | 7/2011 | Korb | G01N 24/08 |
| | | | 324/303 |
| 2011/0181278 A1* | 7/2011 | Chen | G01V 3/32 |
| | | | 324/303 |
| 2013/0091941 A1* | 4/2013 | Huh | E21B 47/1015 |
| | | | 73/152.08 |
| 2013/0113479 A1 | 5/2013 | Chen et al. | |
| 2013/0200890 A1* | 8/2013 | Hursan | G01V 3/32 |
| | | | 324/303 |
| 2013/0257424 A1* | 10/2013 | Holland | G01N 24/081 |
| | | | 324/303 |
| 2013/0261973 A1* | 10/2013 | Li | G01V 3/32 |
| | | | 702/8 |
| 2015/0046092 A1* | 2/2015 | Chok | E21B 49/08 |
| | | | 702/11 |

OTHER PUBLICATIONS

Altunbay et al, "Formation Damage Assessment and Remedial Economics from Integration of NMR and Resistivity Log Data", SPE 84384. Society of Petroleum Engineers, SPE Annual Technical Conference & Exhibition, Oct. 5-8, 2003, Denver, Colorado, 6 pages.

Gandhi et al., "Correction of invasion effects on well logs in Camisea gas reservoirs, Peru, with the constructin of static and dynamic multilayer petrophyiscal models", AAPG Bulletin, vol. 97, No. 3, pp. 379-412, aapgbull. geoscienceworld.org.

van der Zwaag et al., "New Methodology to Investigate Formation Damage Using Non-Destructive Analytical Tools", SPE 38161, SPE European Formation Damage Conference, Jun. 2-3, 1997, The Hague, Netherlands, 13 pages.

* cited by examiner

NMR LOGGING INTERPRETATION OF SOLID INVASION

BACKGROUND

Geologic formations are used for many applications such as hydrocarbon production, geothermal production, and carbon dioxide sequestration. Typically, boreholes are drilled into the formations to provide access to them. Various downhole tools may be conveyed in the boreholes in order to characterize the formations. Characterization of the formations and the fluids within provides valuable information related to the intended use of the formation so that drilling and production resources can be used efficiently.

One type of downhole tool is a nuclear magnetic resonance (NMR) tool that measures the nuclear magnetic properties of formation materials. NMR logging data of unconsolidated sands suggests that solid invasion into the formation may occur. Solid invasion is the phenomenon of fine particles in the drilling mud invading into the formation before or during the forming of mud cake. This phenomenon may also occur for carbonate reservoir. Fine carbonate particles produced from the drilling, especially when a polycrystalline diamond compact (PDC) bit is used, mixes into the mud and may then invade into the formation for some or many carbonate wells with favorable porosity and permeability condition. Because solid invasion can affect NMR measurements of formation materials of interest, it would be well received in the drilling and geophysical exploration industries if the effects of solid invasion could be quantified.

BRIEF SUMMARY

Disclosed is a method for estimating an effect on nuclear magnetic resonance (NMR) measurements of an invasion of solid particles into pores of an earth formation penetrated by a borehole. The method includes: conveying a carrier through the borehole; performing an NMR measurement on a volume of interest in the formation to provide a relaxation time constant using an NMR tool disposed at the carrier; receiving information describing the solid particles in the pores; and quantifying, using a processor, an effect on the measured relaxation time constant due to the invasion of solid particles using the received information.

Also disclosed is an apparatus for estimating an effect on nuclear magnetic resonance (NMR) measurements of an invasion of solid particles into pores of an earth formation penetrated by a borehole, the apparatus comprising: a carrier configured to be conveyed through the borehole; a NMR tool disposed at the carrier and configured to perform a NMR measurement on a volume of interest in the formation to provide a relaxation time constant; and a processor. The processor is configured to receive information describing the solid particles in the pores and quantify an effect on the measured relaxation time constant due to the invasion of solid particles using the received information.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method presented herein by way of exemplification and not limitation with reference to the figures.

Disclosed are apparatus and method estimating an effect on nuclear magnetic resonance (NMR) measurements of an invasion of particles into pores of an earth formation. The effects are quantified so that the output of an NMR tool can be corrected or uncorrected NMR tool output can be compensated for during interpretation by an analyst.

Figure 1:
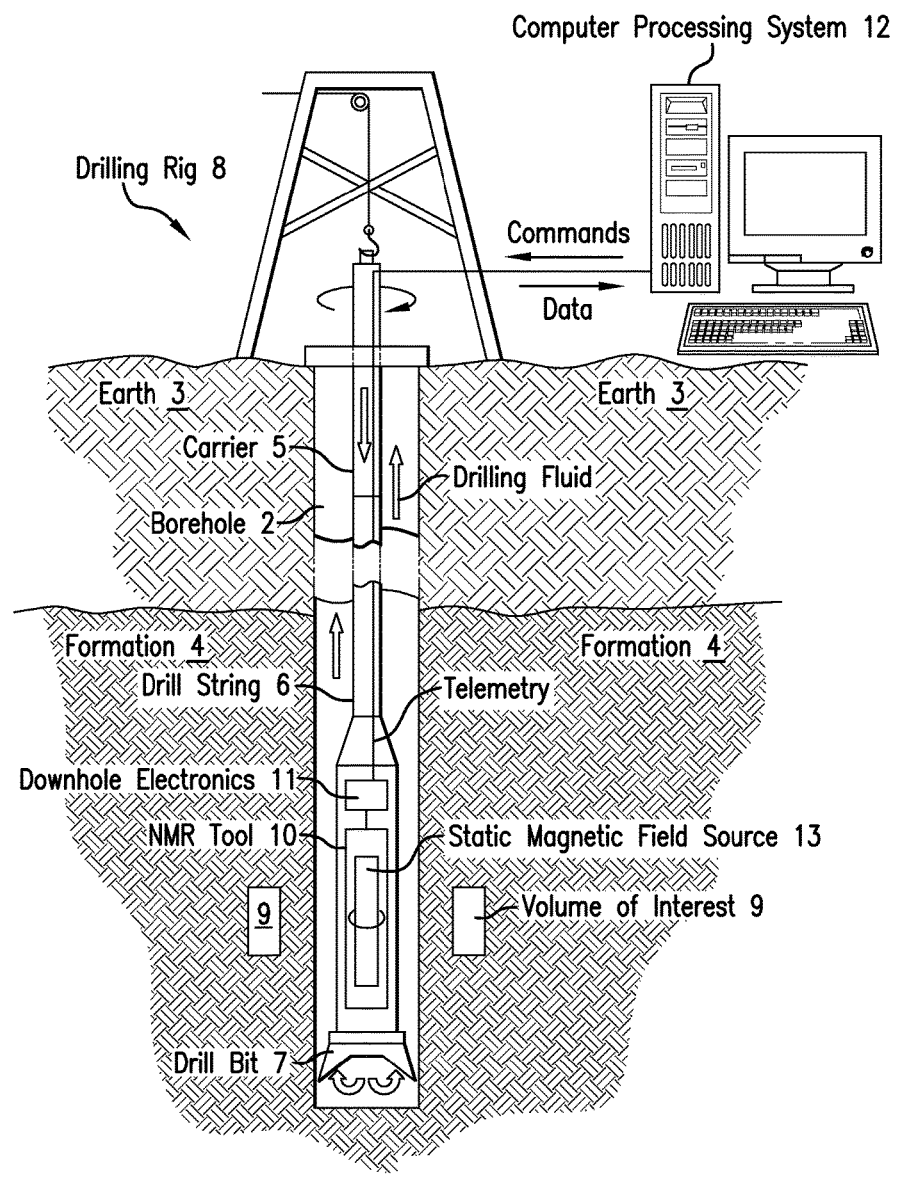
FIG. 1 illustrates a cross-sectional view of an exemplary embodiment of a nuclear magnetic resonance (NMR) tool disposed in a borehole penetrating the earth.

FIG. 1 illustrates a cross-sectional view of an exemplary embodiment of an NMR tool 10 disposed in a borehole 2 penetrating the earth 3, which includes an earth formation 4. The NMR tool 10 is configured to perform NMR measurements on the formation 4. The NMR measurements yield transverse relaxation times $T_2$, which are exponential decay time constants that correspond to a characteristic or property of the formation 4 material. Transverse relaxation relates to the loss of coherent energy by protons in the formation 4 material while precessing about a static magnetic field during an NMR measurement. There is not one single value of $T_2$ for formation rock but a wide distribution of values lying anywhere between fractions of a millisecond and several seconds for example. The distribution of $T_2$ values is the principal output of the NMR tool 10 and may be referred to as an NMR log. Components in the NMR tool 10 includes a static magnetic field source 13 that magnetizes formation materials and an antenna 14 that transmits precisely timed bursts of radio-frequency energy that provides an oscillating magnetic field. In a time period between these pulses, the antenna receives a decaying echo signal from those hydrogen protons that are in resonance with the static magnetic field produced by the static magnetic field source. NMR measurements are performed in a cylindrical volume surrounding the NMR tool 10 referred to as a volume of interest 9. Because a linear relationship exists between the hydrogen proton resonance frequency and the strength of the static magnetic field, the frequency of transmitted radio-frequency energy can be tuned to investigate volumes of interest having different diameters around the NMR tool 10. It can be appreciated that the NMR tool 10 may include a variety of components and configurations as known in the art of NMR. In that NMR tools are known in the art, specific details of components and configurations of these tools are not discussed in further detail.

The NMR tool 10 is conveyed through the borehole 2 by a carrier 5, which can be a drill tubular such as a drill string 6. A drill bit 7 is disposed at the distal end of the drill string 6. A drill rig 8 is configured to conduct drilling operations such as rotating the drill string 6 and thus the drill bit 7 in order to drill the borehole 2. In addition, the drill rig 8 is configured to pump drilling mud (i.e., drill fluid) through the drill string 6 in order to lubricate the drill bit 7 and flush cuttings from the borehole 2. Downhole electronics 11 are configured to operate the NMR tool 10, process measurement data obtained downhole, and/or act as an interface with telemetry to communicate data or commands between downhole components and a computer processing system 12 disposed at the surface of the earth 3. Non-limiting embodiments of the telemetry include pulsed-mud and wired drill pipe for real time communications. System operation and data processing operations may be performed by the downhole electronics 11, the computer processing system 12, or a combination thereof. In an alternative embodiment, the carrier 5 may be an armored wireline, which may also provide communications with the surface processing system 12.

The effects of solid invasion on NMR logging can be twofold: (1) the porosity is underestimated because solids occupy part of the pore space and (2) the NMR $T_2$ and $T_1$ relaxation time constants are shorter than without the solids invasion. As discussed below, solid invasion can affect NMR log measurements significantly when it occurs.

When there is no solid invasion, the NMR $T_2$ relaxation time constant may be represented as follows:

$$\frac{1}{T_2} = \frac{1}{T_2^{bulk}} + \frac{1}{T_2^{diff}} + \frac{1}{T_2^{surf}} \quad (1)$$

where $T_2$ is the overall transverse relaxation time constant, $T_2^{bulk}$ is the bulk relaxation time constant, $T_2^{diff}$ is the diffusion relaxation time constant, and $T_2^{surf}$ is the surface relaxation time constant. The $T_1$ relaxation time may be represented as follows:

$$\frac{1}{T_1} = \frac{1}{T_1^{bulk}} + \frac{1}{T_1^{surf}} \quad (2)$$

where $T_1$ is the overall longitudinal relaxation time constant, $T_1^{bulk}$ is the bulk relaxation time constant, and $T_1^{surf}$ is the surface relaxation time constant. The diffusion relaxation time does not apply for $T_1$.

$T_2^{surf}$ may be expressed in the following relationship:

$$\frac{1}{T_2^{surf}} = \rho \frac{A}{V} \quad (3)$$

where $\rho$, A, and V are the surface relaxivity, pore surface area, and pore volume, respectively. The corresponding equation for $T_1$ is:

$$\frac{1}{T_1^{surf}} = \rho_1 \frac{A}{V} \quad (3')$$

where $\rho_1$ may be different from $\rho$.

In general, solid invasion will not influence the bulk relaxation time constant $T_2^{bulk}$, but it does have an influence on the diffusion relaxation time constant $T_2^{diff}$, which may be smaller due to the decreasing of effective porosity and increasing of tortuosity caused by the invaded particles. However, this influence is generally small compared to the surface relaxation time constant $T_2^{surf}$. Thus, $T_2^{diff}$ is neglected in the following. Also since both $T_2$ and $T_1$ are now governed by the same relaxation mechanisms (i.e. bulk and surface relaxation), the teachings continue by only referring to $T_2$ in the following, although all reasoning applies to $T_1$ as well.

It is assumed that (a) the formation has porosity $\phi$ (i.e., ratio of volume of void space in formation rock to the total volume of the rock), (b) the invading fluid (i.e., drilling mud) having solid particles dominates the formation fluid, and (c) the drilling mud and the formation fluid are miscible (i.e., water zone for water based mud or oil zone for oil based mud). If the drilling mud and the formation fluid are not miscible, then solid invasion will have little or no effects on the majority of the fluid in the formation due to limited or no invasion fluid to solid surface contact.

Figure 2:
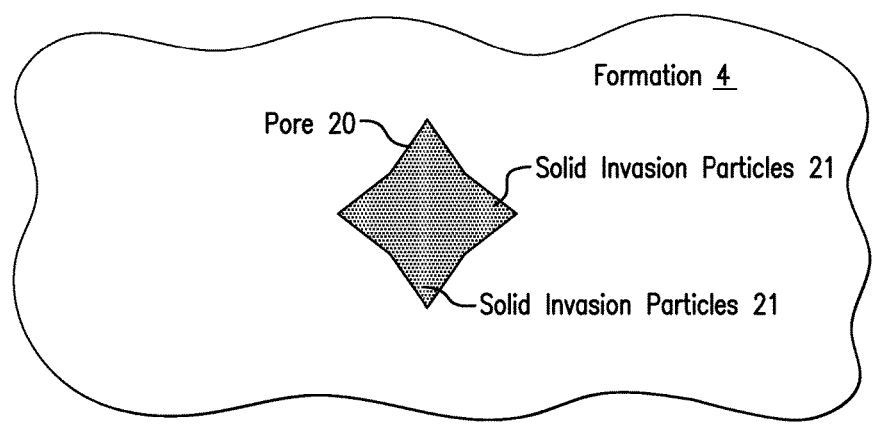
FIG. 2 depicts aspects of a pore invaded with fine solids to form a uniform suspension.

Referring to FIG. 2, a homogeneous suspension of solid invasion particles 21 in a pore 20 in the formation 4 is illustrated after solid invasion. The pore 20 is just one of many pores in the formation 4. Assuming the total volume of all the solid invasion particles is represented as $\phi_s$ (expressed in porosity units) and each of the particles is spherical with radius r, then $\phi_s$ may be calculated as follows:

$$\phi_s = \phi \cdot n \cdot \frac{4}{3}\pi r^3 \quad (4)$$

where n is the number density or number of particles in a unit pore volume.

The porosity measured from the NMR log ($\phi_{log}$) is expressed in equation (5).

$$\phi_{log} = \phi - \phi_s = \phi\left(1 - \frac{4}{3}n\pi r^3\right) \quad (5)$$

The solid invasion particles contribute a surface relaxation mechanism to the fluid in the pore. Considering that the volume of the pore illustrated in FIG. 2 is V, then the number of solid invasion particles N in that pore is expressed in equation (6).

$$N = n \cdot V \quad (6)$$

It follows that the total surface area of all the solid invasion particles in the pore ($A_s$) can be expressed using equation (7).

$$A_s = (Vn) \cdot 4\pi r^2 \quad (7)$$

Further, it follows that the total volume of the fluid in the pore ($V_f$) is the total void space or volume of the pore minus the total volume of all the solid invasion particles in the pore as expressed in equation (8).

$$V_f = V\left(1 - \frac{4}{3}\pi r^3\right) \quad (8)$$

Finally, considering that the invasion solid particles may have different surface relaxivity from that of the pore surface, the surface relaxation time constant term in equation (2) for fluid within the pore may be expanded as follows:

$$\frac{1}{T_{2,SI}^{surf}} = \rho \frac{A}{V_f} + \rho_s \frac{A_s}{V_f} \quad (9)$$

where the subscript SI indicates surface relaxation $T_2$ with invasion of solid particles and $\rho_s$ is the surface relaxivity of the solid invasion particles. Equation (9) shows that solids invasion modifies the fluid relaxation time in two ways.

First, it enhances the pore surface relaxation contribution by decreasing the fluid volume from V to $V_f$ while exposing to the same pore surface area A, as indicated by the first term on the right side. Second, the invasion solid itself contributes a surface relaxation mechanism as shown in the second term on the right in Eq. (9).

Equations (5), (7) and (8) may be inserted into equation (9) to derive equation (10).

$$\frac{1}{T_{2,SI}^{surf}} = \left(\frac{1}{T_2^{surf}} + \rho_s n 4\pi r^2\right)\frac{\phi}{\phi_{log}} \quad (10)$$

Using the relationship in equation (5), the density n can be removed from equation (10) to arrive at equation (11).

$$\frac{1}{T_{2,SI}^{surf}} = \left(\frac{1}{T_2^{surf}} + \rho_s \frac{3}{r}\frac{\phi_s}{\phi}\right)\frac{\phi}{\phi_{log}} \quad (11)$$

Equation (11) can be rewritten as equation (12) where $R_{SI}=\phi_s/\phi$, the ratio of invaded porosity to the total porosity.

$$\frac{1}{T_{2,SI}^{surf}} = \frac{1}{T_2^{surf}}\frac{1}{1-R_{SI}} + \rho_s\frac{3}{r}\frac{R_{SI}}{1-R_{SI}} \quad (12)$$

Note that the factor 3/r represents the surface area-to-volume ratio $A_s/V_s$ of the solids and depends on their shape. While a sphere results in a surface-to-volume ratio of 3/r, a cube will yield 6/a or tetrahedron 6*sqrt(6)/a where a represents the side length. Depending on the shape of the solids, the surface-to-volume ratio has to be adjusted accordingly.

Next, some special cases are considered. In case 1, the solid invasion particles have minimum or negligible (e.g., ≤5%) surface relaxation compared to that of the formation fluid in the pores. For example, consider carbonate reservoir having an oil zone and the solid invasion particles are carbonate powder freshly ground by the drilling bits. These freshly ground carbonate "particles" are water wet on the surface and, therefore, have minimum contribution to the relaxation of oil in the pores. Thus, equation (10) may be simplified to equation (13).

$$T_{2,SI}^{surf} = T_2^{surf}\frac{\phi_{log}}{\phi} \quad (13)$$

Eq. (13) indicates in this special case that the measured $T_2$ is directly proportional to the ratio of remaining pore space to the original pore space. For example, if solid invasion particles occupy 20% of the pore space, the remaining porosity is 80% of the real porosity; the measured $T_2$ is reduced to 80% of its original value as well. An interesting derivative is that if these solid particles are flushed out later time and relog is followed, the NMR measurements will indicate a larger porosity and the measured NMR $T_2$ will also be longer.

In case 2, the condition of the solid invasion particles dominating the measured fluid relaxation time is considered. That is, bulk relaxation and pore surface relaxation are negligible (e.g., ≤5%) compared to the surface relaxation of the solid particles. From Eq. (11), invaded solids dominate the relaxation of pore fluid when equation (14) is satisfied. In one or more embodiments, the symbol ">>" relates to the lesser value being 10% or less of the greater value.

$$\rho_s \frac{3}{r}\frac{\phi_s}{\phi-\phi_s} >> \frac{1}{T_2^{surf}} \quad (14)$$

Considering light oil or water in large pores, then the right side of equation (14) is equal to or smaller than one. Accordingly, equation (14) then requires the relationship in equation (15).

$$\frac{\rho_s}{r}\frac{1}{(\phi/\phi_s)-1} >> \frac{1}{3} \quad (15)$$

For sandstone in general, $\rho_s \sim 1.6\times10^{-5}$ m/s; and a 20% solid invasion would only require $r<<1.2\times10^{-5}$ m to satisfy equation (14). A 5% solid invasion with particle size 0.1 μm will also approximately satisfy equation (14). Apparently this condition in the field can be easily satisfied. Furthermore, if the invaded solid particles have paramagnetic minerals with a much larger surface $\rho_s$, then a solid invasion of less than 1%, which does not have a measurable effects on the porosity, can still have a significant influence on the transverse relaxation time constant ($T_2$) and also the longitudinal relaxation time constant ($T_1$) of pore fluids.

Figure 3A:
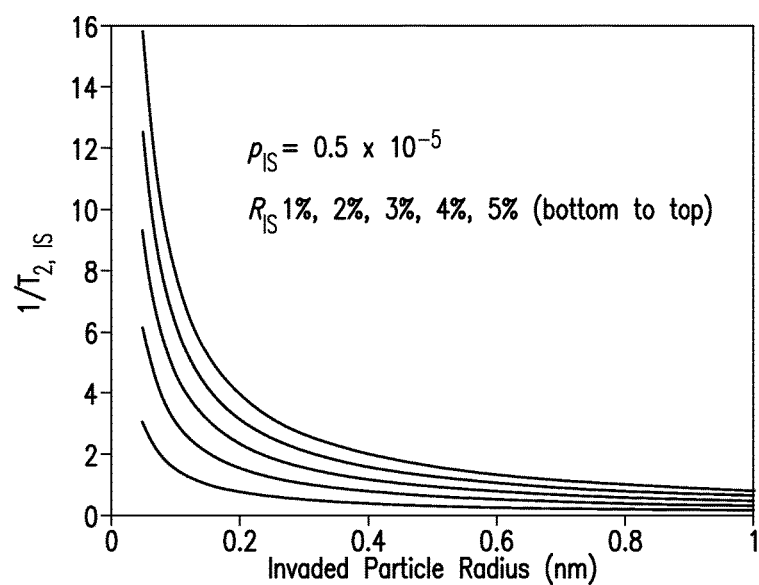
FIGS. 3A, 3B, and 3C, collectively referred to as FIG. 3, depict aspects
Figure 3B:
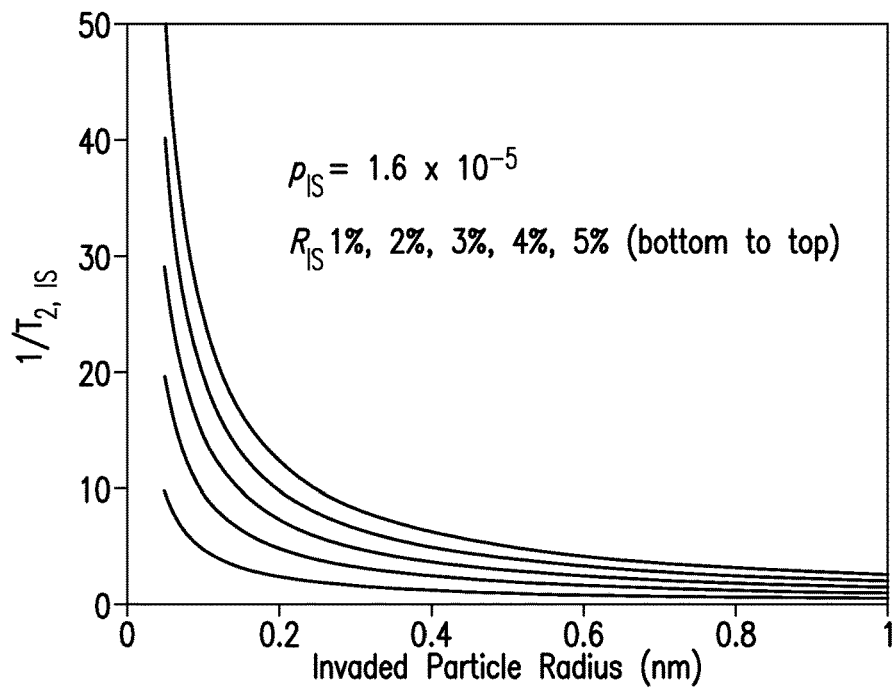
Figure 3C:
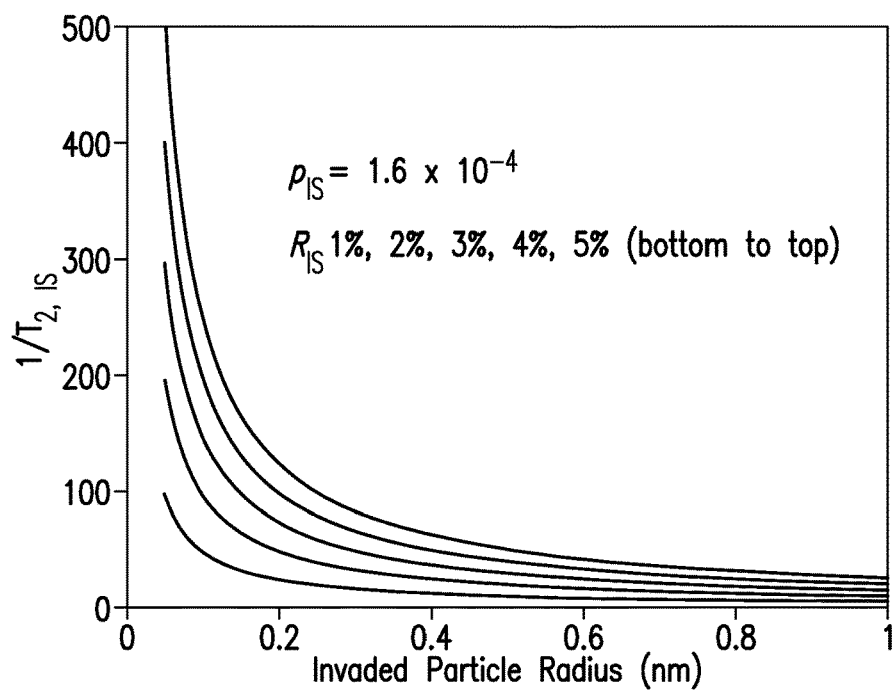

FIG. 3 depicts aspects of the surface relaxation time constant due to invaded solids in the fluids in the pores according to the particle radius calculated for different surface relaxivity values. In FIG. 3A, the solid invasion particles are carbonate and $\rho_s=0.5\times10^{-5}$ m/s. In FIG. 3B, the solid invasion particles are sandstone and $\rho_s=1.6\times10^{-5}$ m/s. And, in FIG. 3C, the solid invasion particles are rock containing paramagnetic minerals and $\rho_s=1.6\times10^{-4}$ m/s.

It can be appreciated that by using the above equations, a processor may provide compensation for solid invasion by outputting a true value of a property of interest. What is wanted is the distribution of transverse relaxation time constants $T_2$'s that relate to the pores in the formation that are considerably away from the borehole and, thus, do not have solid invasion. From the $T_2$'s of the pores without solid invasion, the actual porosity of the formation may be determined. However, the solid invasion particles distort or modify the measured $T_2$'s affecting the determination of the true properties of the formation away from the borehole. As shown in equation (1), the measured $T_2$ is affected by three relaxation components—bulk, diffusion, and surface. Depending on the composition and/or physical properties of the solid invasion particles, the surface relaxation component may be affected the most by the solid invasion particles. The surface relaxation component affected by solid invasion is referred to as $T_{2,SI}^{surf}$. Equations (10)-(12) relate $T_{2,SI}^{surf}$ to $T_2^{surf}$, which is the surface relaxation component if solid invasion particles were not present in the pores. In general, other variables are required to determine the relationship between $T_{2,SI}^{surf}$ and $T_2^{surf}$ using equations (12)-(11) such as the radius or average radius of the solid invasion particles, the surface relaxivity of those particles, and the ratio of porosity occupied by solids to the total porosity of the pores being evaluated by the NMR tool 10 for example. Values of these other variables may be obtained from previously obtained data, from laboratory analysis of the actual particles downhole during the NMR measurements, laboratory analysis of particles similar to those particles expected downhole, and measurements using other types of downhole tools such as neutron tools for example. Once $T_{2,SI}^{surf}$ is quantified, its effect on the measured $T_2$'s can also be quantified using equation (1) for example. By removing the influence of $T_{2,SI}^{surf}$ from the measured $T_2$'s, output from the NMR tool 10 can be compensated, by a processor for example, to provide the true $T_2$'s that relate to pores deeper in the formation that do not have solid invasion. In one or more embodiments, the influence of $T_{2,SI}^{surf}$ is removed by subtracting its inverse from the right side of equation (1) as the magnitude of the inverse of $T_{2,SI}^{surf}$ is generally much greater than the inverse of $T_2^{surf}$. Alternatively, if uncompensated NMR tool output is being analyzed, then the quantification can be used to help interpret the uncompensated NMR data obtained from an NMR tool such as by applying a correction that would negate the influence of the solid invasion particles.

It can be appreciated that porosity is just one property that may be determined using the transverse relaxation time constants that are compensated for invasion of solid particles in pores near the borehole containing the NMR tool. The techniques disclosed herein may also be used to improve the accuracy in determining other formation properties from distributions of measured transverse and/or longitudinal relaxation time constants. Other properties may include reservoir permeability and hydrocarbon typing, which includes differentiating between different types of fluids and identifying a type of hydrocarbon present in the formation. These other properties may be determined using known relationships that relate a property of interest to a distribution of relaxation time constants.

Figure 4:
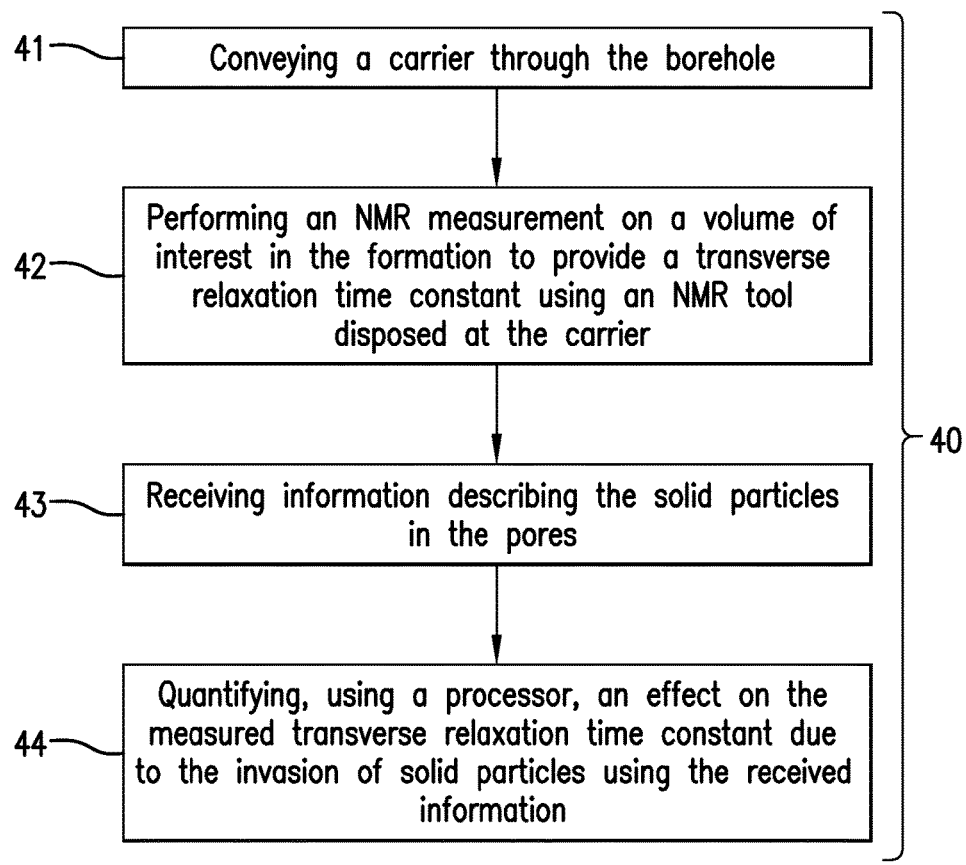
FIG. 4 is a flow chart of a method estimating an effect on nuclear magnetic resonance (NMR) measurements of an invasion of solid particles into pores of an earth formation penetrated by a borehole.

FIG. 4 is a flow chart for a method 40 for estimating an effect on nuclear magnetic resonance (NMR) measurements of an invasion of solid particles into pores of an earth formation penetrated by a borehole. Block 41 calls for conveying a carrier through the borehole. Block 42 calls for performing an NMR measurement on a volume of interest in the formation to provide a relaxation time constant using an NMR tool disposed at (i.e., in or on) the carrier. The relaxation time constant may include a transverse relaxation time constant and/or a longitudinal time constant. Block 43 calls for receiving information describing the solid particles in the pores. The information may be received using a processor. The received information may include at least one of a size of each of the particles, a surface relaxivity of each of the particles, an amount of space the particles occupy in each of the pores, and a surface area-to-volume ratio of the particles. This information may be pre-known or it may be calculated from other information or data. Block 44 calls for quantifying, using a processor, an effect on the measured transverse relaxation time constant due to the invasion of solid particles using the received information. The method 40 may also include calculating the transverse relaxation time constant $T_2$'s for pores away from the borehole not having solid invasion using the $T_2$'s measured by the NMR tool and the transverse surface relaxation time constant $T_{2,SI}^{surf}$. The method 40 may also include displaying the quantified effect or the calculated $T_2$'s for pores away from the borehole not having solid invasion using a user interface such as a display as the one in the computer processing system 12. The method 40 may also include using the quantified effect to improve the accuracy in determining a formation property for pores not having solid invasion away from the borehole. By knowing the quantified effect, the quantified effect can be compensated for in processes for estimating a formation property using relaxation time constants obtained by an NMR tool probing a formation. Non-limiting examples of formation properties estimated from relaxation time constants include porosity, permeability, and hydrocarbon typing. In that processes for estimating formation properties using relaxation time constants are known in the art, these processes are not discussed in further detail.

In support of the teachings herein, various analysis components may be used, including a digital and/or an analog system. For example, the downhole electronics 11 or the computer processing system 12 may include digital and/or analog systems. The system may have components such as a processor, storage media, memory, input, output, communications link (wired, wireless, pulsed mud, optical or other), user interfaces (e.g., a display), software programs, signal processors (digital or analog) and other such components (such as resistors, capacitors, inductors and others) to provide for operation and analyses of the apparatus and methods disclosed herein in any of several manners well-appreciated in the art. It is considered that these teachings may be, but need not be, implemented in conjunction with a set of computer executable instructions stored on a non-transitory computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a power supply (e.g., at least one of a generator, a remote supply and a battery), cooling component, heating component, magnet, electromagnet, sensor, electrode, transmitter, receiver, transceiver, antenna, controller, optical unit, electrical unit or electromechanical unit may be included in support of the various aspects discussed herein or in support of other functions beyond this disclosure.

The term "carrier" as used herein means any device, device component, combination of devices, media and/or member that may be used to convey, house, support or otherwise facilitate the use of another device, device component, combination of devices, media and/or member. Other exemplary non-limiting carriers include drill strings of the coiled tube type, of the jointed pipe type and any combination or portion thereof. Other carrier examples include casing pipes, wirelines, wireline sondes, slickline sondes, drop shots, bottom-hole-assemblies, drill string inserts, modules, internal housings and substrate portions thereof.

Elements of the embodiments have been introduced with either the articles "a" or "an." The articles are intended to mean that there are one or more of the elements. The terms "including" and "having" are intended to be inclusive such that there may be additional elements other than the elements listed. The conjunction "or" when used with a list of at least two terms is intended to mean any term or combination of terms. The term "coupled" relates to one component being coupled to another component either directly or indirectly via an intermediate component.

While one or more embodiments have been shown and described, modifications and substitutions may be made thereto without departing from the spirit and scope of the invention. Accordingly, it is to be understood that the present invention has been described by way of illustrations and not limitation.

It will be recognized that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood that various changes may be made and equivalents may be substituted for elements thereof without departing from the scope of the invention. In addition, many modifications will be appreciated to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for estimating an effect on nuclear magnetic resonance (NMR) measurements of an invasion of solid particles into pores of an earth formation penetrated by a borehole, the method comprising:
   conveying a carrier through the borehole;
   performing an NMR measurement on a volume of interest in the formation to provide a relaxation time constant using an NMR tool disposed at the carrier;
   receiving information describing the solid particles in the pores, the solid particles comprising fine particles of formation material produced from drilling the borehole, the information comprising a shape property of the solid particles;
   quantifying, using a processor, the effect on the measured relaxation time constant due to the invasion of the solid particles using the received information;
   correcting the NMR measurement by the processor using the quantified effect to provide corrected NMR output; and
   operating drilling or production resources in response to a parameter of the earth formation determined from the corrected NMR output having a value that provides input for operating the drilling or production resources.

2. The method according to claim 1, wherein the relaxation time constant comprises at least one of a transverse relaxation time constant and a longitudinal relaxation time constant.

3. The method according to claim 1, wherein the information comprises at least one selection from a group consisting of a size of each of the particles, a surface relaxivity of each of the particles, and an amount of space the particles occupy in each of the pores.

4. The method according to claim 1, wherein the solid invasion particles have negligible surface relaxation compared to the surface relaxation of formation fluid in the pores.

5. The method according to claim 4, wherein quantifying comprises using the following relationship:

$$T_{2,SI}^{surf} = T_2^{surf} \frac{\phi_{log}}{\phi}$$

where $T_{2,SI}^{surf}$ is the surface transverse relaxation time constant with solid invasion, $T_2^{surf}$ is the surface transverse relaxation time constant without solid invasion, $\phi_{log}$ is the porosity determined from the NMR measurement, and $\phi$ is the actual porosity of formation.

6. The method according to claim 1, wherein bulk relaxation and pore surface relaxation are negligible compared to the surface relaxation of the solid particles.

7. The method according to claim 6, further comprising calculating a surface relaxation time constant for pores having the invasion of solid particles.

8. The method according to claim 7, wherein calculating a surface relaxation time constant for pores comprises using the following relationship:

$$\frac{1}{T_{2,SI}^{surf}} = \rho_s \frac{A_s}{V_s} \frac{\phi_s}{\phi_{log}}$$

where $T_{2,SI}^{surf}$ is the surface transverse relaxation time constant of the invaded solid particles, $\phi_{log}$ is the porosity determined from the NMR measurement, $\phi_s$ is the porosity occupied by the solid particles, $\rho_s$ is the surface relaxivity of the solid invasion particles, and $A_s/V_s$ represents the surface area-to-volume ratio of the solid particles.

9. The method according to claim 8, wherein at least a portion of the solid particles are modeled as a sphere and $A_s/V_s$ is 3/r where r is the radius of the sphere.

10. The method according to claim 1, further comprising using the quantified effect to improve the accuracy in determining a formation property for pores not having solid invasion away from the borehole.

11. The method according to claim 10, wherein the formation property is at least one of porosity, permeability, and hydrocarbon typing.

12. A method for estimating an effect on nuclear magnetic resonance (NMR) measurements of an invasion of solid particles into pores of an earth formation penetrated by a borehole, the method comprising:
   conveying a carrier through the borehole;
   performing an NMR measurement on a volume of interest in the formation to provide a relaxation time constant using an NMR tool disposed at the carrier;
   receiving information describing the solid particles in the pores; and
   quantifying, using a processor, an effect on the measured relaxation time constant due to the invasion of the solid particles using the received information;
   correcting the NMR measurement by the processor using the quantified effect to provide corrected NMR output; and
   operating drilling or production resources in response to a parameter of the earth formation determined from the corrected NMR output having a value that provides input for operating the drilling or production resources;
   wherein quantifying comprises solving:

$$\frac{1}{T_{2,SI}^{surf}} = \frac{1}{T_2^{surf}} \frac{1}{1-R_{SI}} + \rho_s \frac{A_s}{V_s} \frac{R_{SI}}{1-R_{SI}}$$

where $T_{2,SI}^{surf}$ is the surface transverse relaxation time constant with solid invasion, $T_2^{surf}$ is the surface transverse relaxation time constant without solid invasion, $R_{SI}$ is the ratio of porosity occupied by solids to the total porosity, $\rho_s$ is the surface relaxivity of the solid invasion particles, and $A_s/V_s$ represents the surface area-to-volume ratio of the solid particles.

13. The method according to claim 12, wherein at least a portion of the solid particles are modeled as a sphere and the surface-to volume ratio factor is $3/r$ where r is the radius of the sphere.

14. The method according to claim 12, further comprising calculating a transverse relaxation time constant for pores without solid invasion away from the borehole using $T_{2,SI}^{surf}$.

15. The method according to claim 14, wherein calculating a transverse relaxation time constant for pores without solid invasion away from the borehole comprises solving the following equation:

$$\frac{1}{T_2} = \frac{1}{T_2^{bulk}} + \frac{1}{T_2^{diff}} + \frac{1}{T_{2,SI}^{surf}}.$$

16. An apparatus for estimating an effect on nuclear magnetic resonance (NMR) measurements of an invasion of solid particles into pores of an earth formation penetrated by a borehole, the apparatus comprising:
   a carrier configured to be conveyed through the borehole;
   a NMR tool disposed at the carrier and configured to perform a NMR measurement on a volume of interest in the formation to provide a relaxation time constant; and
   a processor configured to:
      receive information describing the solid particles in the pores, the solid particles comprising fine particles of formation material produced from drilling the borehole, the information comprising a shape property of the solid particles;
      quantify an effect on the measured relaxation time constant due to the invasion of solid particles using the received information;
      correct NMR measurements using the quantified effect to provide corrected NMR output;
   a drilling or production resource configured to be operated in response to a parameter of the earth formation determined from the corrected NMR output having a value that provides input for operating the drilling or production resources.

17. The apparatus according to claim 16, wherein the relaxation time constant comprises at least one of a transverse relaxation time constant and a longitudinal relaxation time constant.

18. The apparatus according to claim 16, wherein the processor is further configured to calculate a surface transverse relaxation time constant $T_{2,S}$ for pores with invasion of solid particles using $T_{2,SI}^{surf}$, where $T_{2,SI}^{surf}$ is the surface transverse relaxation time constant of the invaded solid particles.

19. The apparatus according to claim 18, wherein the processor is further configured to calculate a transverse relaxation time constant $T_2$ for pores without solid invasion away from the borehole using $T_{2,SI}^{surf}$.

20. The apparatus according to claim 16, wherein the processor is further configured to estimate a formation property with improved accuracy using the quantified effect.

* * * * *